United States Patent [19]

Virag et al.

[11] Patent Number: 5,546,936
[45] Date of Patent: Aug. 20, 1996

[54] TRACHEAL TUBE WITH REINFORCED FLEXIBLE SEGMENT

[75] Inventors: Robert A. Virag, Chesterfield, Mo.; Richard V. Nye, Laguna Hills, Calif.; Duane L. Horton, St. Louis, Mo.

[73] Assignee: Mallinckrodt Medical, Inc., St. Louis, Mo.

[21] Appl. No.: 336,139

[22] Filed: Nov. 8, 1994

Related U.S. Application Data

[63] Continuation-in-part of Ser. No. 124,829, Sep. 21, 1993, which is a continuation of Ser. No. 885,691, May 19, 1992, Pat. No. 5,245,992.

[51] Int. Cl.⁶ .................................................. A61M 16/00
[52] U.S. Cl. ........................ 128/207.14; 128/200.26
[58] Field of Search ................... 128/200.26, 207.14, 128/207.15

[56] References Cited

U.S. PATENT DOCUMENTS

| | | | |
|---|---|---|---|
| 3,363,629 | 1/1968 | Kuhn | 604/281 |
| 3,599,642 | 8/1971 | Tindel | 128/207.14 |
| 3,964,488 | 6/1976 | Ring et al. | 128/207.14 |
| 4,050,466 | 9/1977 | Koerbacher | 128/207.14 |
| 4,378,796 | 4/1983 | Milhand | 128/207.15 |
| 4,622,965 | 11/1986 | Teeple | 128/207.14 |
| 5,024,220 | 6/1991 | Holmgreen et al. | 128/200.26 |
| 5,065,757 | 11/1991 | Dragisic et al. | 128/207.15 |
| 5,217,008 | 6/1993 | Lindholm | 128/207.14 |
| 5,245,992 | 9/1993 | Nye | 128/207.14 |

*Primary Examiner*—Aaron J. Lewis
*Attorney, Agent, or Firm*—David A. Hey

[57] ABSTRACT

The present invention relates to a specialized tracheal tube and a method of using such for introduction of gasses or vapors along the trachea, such as by an anesthesiologist during the administration of anesthesia to a patient undergoing surgery. In particular, the present invention relates to a tracheal tube having a filament reinforced flexible portion that allows for movement of the proximal end relative to the distal end of the tracheal tube without creating stress at the proximal or distal ends. The tracheal tube according to the present invention allows 360° access to the head and neck area of a patient, and allows for movement of the proximal end of the tracheal tube during a surgical procedure without requiring re-intubation.

8 Claims, 1 Drawing Sheet

TRACHEAL TUBE WITH REINFORCED FLEXIBLE SEGMENT

This is a continuation-in-part application of U.S. Ser. No. 08/124,829, filed Sep. 21, 1993, still, which is a continuation application of U.S. Ser. No. 07/885,691, filed May 19, 1992, now U.S. Pat. No. 5,245,992.

BACKGROUND

The present invention relates to a method of using specialized equipment for medical use. The present invention particularly relates to the use of a specialized tracheal tube for introduction of gasses or vapors along the trachea. For example, a tracheal tube used by an anesthesiologist during the administration of anesthesia to a patient undergoing surgery.

As early as 1889, a straight tracheal tube was reported as being used to administer anesthesia. From that time, tracheal tubes have been designed of various shapes and curvatures and have been made of either rigid or flexible materials. Flexible tubes have the advantage of automatically conforming to the shape and curvature of the body in individual instances, but have the disadvantage of dangerous kinking which may cause critical stoppage of gas or vapor flow through the tube.

Known tracheal tubes include the so-called "Oxford tube", which has a widely curved, right-angle bend adapted for placement in the trachea and posterior pharynx, and is formed of non-kinking, flexible tubing. A similarly constructed tube having a sigmoid curve is shown in U.S. Pat. No. 3,363,629, to Kuhn. Neither of these tubes are entirely satisfactory.

When surgery is to be performed on the head, face, mouth or neck areas of a patient, it is desirable to provide a maximum amount of access to those areas. Therefore, placement of the anesthesia circuit becomes very important.

The anesthesia circuit is normally comprised of a tracheal tube, an anesthesia supply and means for connecting the tracheal tube to the anesthesia supply. Several different arrangements of the anesthesia circuit have been used in an attempt to maximize access to the surgical area.

Tracheal tubes may be designed so as to be either inserted through the oral or nasal passages of a patient. The choice of using an oral or nasal tracheal tube is generally dependent on the type of medical or surgical procedure to be performed.

Oral tracheal tubes are introduced through the patient's mouth and directed into the patient's trachea. Oral tracheal tubes are generally preferred over nasal tracheal tubes because it is felt they are easier to place correctly in the trachea.

A nasal tracheal tube is a tube which is introduced through the patient's nose and directed into the patient's trachea. Nasal tracheal tubes are used when the surgeon performs surgery in the mouth, when the mouth must be closed during surgery, or when the patient must continue to be mechanically ventilated for long periods after the surgical procedure.

One known type of tracheal tube is designed to have a proximal end which terminates near its exit from the mouth or nose of a patient. Connector tubing is then used to connect the tracheal tube to the anesthesia supply.

A connector for a tracheal tube of this type is described in U.S. Pat. No. 5,024,220 to Holmgreen et al. The connector described in Holmgreen et al comprises a section of flexible corrugated tubing which has a distal end adapted to fit into the lumen of an intubated nasal tracheal tube, and a proximal end adapted to receive a standard anesthesia tubing connector. The connector described in Holmgreen et al is intended to facilitate access to the mouth and face of a patient and to reduce the possibility of trauma or tissue damage during intubation and use.

However, the connector and tracheal tube combination of Holmgreen et al has several disadvantages. For example, the connector of Holmgreen et al requires numerous connection points to complete the anesthesia circuit. Each connection point of this type, i.e. non-permanent, carries the risk of leakage or disconnection during use, thereby compromising the anesthesia circuit. In addition, the corrugated tubing used as the connector has a rough, ribbed inner surface, which makes it difficult to pass accessory equipment, such as a fiber optic scope or suction catheter, for example, through the tube. In particular, passage of such a device may often be impeded by the corrugated ribbing of the connector, thereby requiring re-maneuvering of the device, as well as use of force to get the device fully through the corrugated segment. Use of such force may cause trauma to the patient's mucosa and trachea, as well as possibly compromising the anesthesia circuit by dislodging the tracheal tube from its proper intubated position. Another disadvantage of using corrugated connector tubing, as described in Holmgreen et al, is that the corrugated tubing possesses shape retention properties. Therefore, the corrugated tubing tends to return to its preformed, non-bent or non-curved state. This can be disadvantageous because the tube in attempting to return to its preformed shape, may loosen or pull free from surgical tape intended to hold it in a secure position. Further, the force exerted to hold the corrugated segment in a curved position, i.e. along the patient's face, is transmitted to the proximal end of the tracheal tube and may cause necrosis at the naris.

A second type of tracheal tube has a preformed proximal end which includes an extension segment that extends from the point of exit from the nose or mouth of the patient and is bent or curved in such a manner to extend along the patient's face to a connection with the anesthesia circuit.

A known tracheal tube for either oral or nasal use and having a preformed proximal end segment, is described in U.S. Pat. No. 3,964,488 to Ring et al. This tube includes a distal or patient end portion which is curved so as to conform to the shape of the trachea and posterior pharynx, an intermediate portion connected to the distal end portion, and a proximal or machine end portion which includes an abrupt bend of no greater than 90°, such that the proximal end portion will be located exteriorly of the patient, and will extend along the face of the patient when the tube is installed for use. In those embodiments where the tube is intended for oral use, the distal or patient end portion extends in the same general direction as the proximal or machine end portion. In those embodiments where the tube is intended for nasal use, the distal or patient end portion extends in the generally opposite direction to the proximal or machine end portion. This tube allows the placement of connectors and adapters away from the surgery area and thereby provides increased access to the head and neck area during surgery. Also, this tube reduces the risk of kinking at the bend location, and helps to prevent injury to the patient from pressure by relatively heavy connectors and adapters attached to the tube.

However, preformed tubes of this type exhibit several disadvantages also. In particular, the curve of the preformed tubes must be controlled accurately to correspond with the anatomy of the patient. While standard sizes and shapes will be appropriate for most patients, there are many occasions when the predetermined curve will leave the proximal extension at an improper distance from the facial region. This may result in excessive pressure being exerted on sensitive tissue in the nasal and oral regions, as well as to the mucosa and trachea at the distal end of the tracheal tube. To avoid such problems, removal of the tracheal tube and re-intubation may be required, which increases the risk of injury or trauma to the patient. If the distance between the face and tube is too great, the assembly may become quite bulky and interfere with surgical access to the operative field.

Also, the preformed tracheal tubes do not allow for shifting of the tube during an operation, but rather may be positioned in only one way. Therefore, full access to the operative field may be compromised.

Therefore, there remains a need for a tracheal tube which allows even greater access to the head and neck of a patient during surgery, and which allows for changing placement of the proximal end of the tube during surgery, without increasing the risk of injury or trauma to the patient.

OBJECTS OF THE INVENTION

It is one object of the present invention to provide a method of using an improved tracheal tube which enables greater access to the head and neck of a patient during surgery, wherein the proximal end of the tracheal tube is capable of being shifted or moved during use without requiring disconnection of the anesthesia circuit or re-intubation of the patient.

SUMMARY OF THE INVENTION

The above objects and others are accomplished according to the present invention by providing a method of using a specialized tracheal tube in such a manner that allows easy relocation of the proximal end of the tube without requiring disconnection of the anesthesia circuit or re-intubation of the patient. The tracheal tube particularly includes at least two sections, wherein at least one section is formed of flexible material which allows the proximal end of the tube to be easily moved and located in an infinite number of positions.

DETAILED DESCRIPTION OF THE INVENTION

Figure 1:
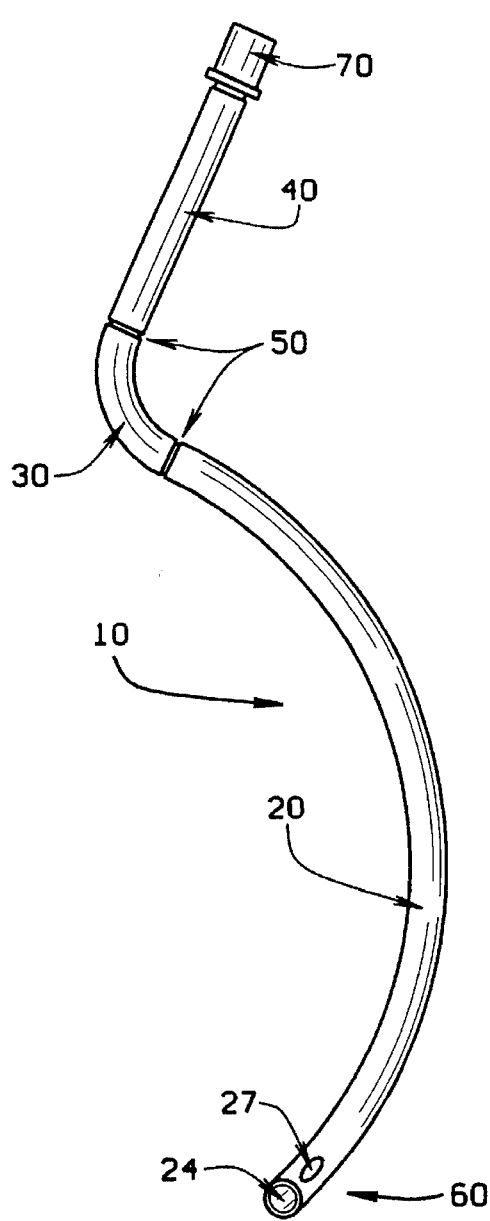
FIG. 1 is a plan view of a first embodiment of the tracheal tube according to the present invention.

The present invention relates to an improved tracheal tube for use during anesthesia of a patient, especially during head, facial, oral, and/or neck surgery. In particular, the tracheal tube according to the present invention is designed in a manner that allows 360 degree access to the head, and neck area of a patient, and allows for easy movement of the proximal end of the tracheal tube to any desired position during surgery. By allowing easy relocation of the proximal end of the tracheal tube, full surgical access is provided to all areas of the head, face, mouth, and/or neck of a patient undergoing surgery.

It is desirable to maximize access to the face and mouth of a patient during surgical procedures for the head, face or neck areas. A common problem associated with providing the maximum access is placement of the anesthesia circuit. The anesthesia circuit includes a tracheal tube, an anesthesia supply and means such as tubing for connecting the tracheal tube to the anesthesia supply.

While oral tracheal tubes are usually preferred for establishing proper placement within the trachea, it is often desirable to use nasal tracheal tubes to provide greater access to the face and mouth of a patient, and also permit closure of the mouth during a surgical procedure. However, current designs of both nasal and oral tracheal tubes have disadvantages as will be discussed below in greater detail.

One current design for a tracheal tube is that described in U.S. Pat. No. 3,964,488 (the RAE tube) as noted above. While this tube has been used successfully by surgeons and anesthesiologists during head and neck surgeries, there are several limitations involved in using this tube. In particular, the nasal version of the tube exits the nose of the patient and then is directed over the nose and forehead to be connected to the anesthesia circuit usually located straight off of the patient's head.

The normal connection of the nasal version of the RAE tube to the anesthesia circuit greatly reduces the access to the patient's head and neck area, as the circuit and anesthesiologist will normally be located at the top of the head. This is often a position which the surgeon needs to occupy in order to successfully complete an operation. The competition for space may therefore prove very frustrating to both the surgeon and the anesthesiologist.

One way of overcoming the placement of the anesthesia circuit at the top of the head, is to curve the anesthesia circuit around the back of the head of the patient and then use connector tubing to run down the patient's side and to the anesthesia machine which may be located at the patient's waist. This has the disadvantage of requiring multiple circuit connectors which pose the greatest risk of circuit disconnect.

The oral version of the RAE tube has the advantage of exiting the mouth of the patient and then being directed down over the chin and eventually being connected to the anesthesia machine located near the feet of the patient. However, oral tracheal tubes can not be used successfully when surgery is carried out in the mouth or in procedures which require the mouth to be closed during surgery, 0such as having the teeth of the patient wired together.

A further disadvantage of both the oral and nasal RAE tubes, as well as other tracheal tubes is the inability to relocate the proximal end of the tracheal tube following intubation. In particular, standard tracheal tubes are not flexible and therefore once intubated, must remain in a fixed position relative to the patient's head and neck. This may prove very disadvantageous if it becomes necessary during surgery to gain access to facial or neck areas that are covered by the tracheal tube.

The tracheal tube according to the present invention overcomes all of the disadvantages noted above, by providing a tracheal tube which includes a segment of flexible tubing on the proximal end, the flexible tubing allowing for full 360° rotation of the proximal end relative to the distal end of the tracheal tube. Further aspects and details of the present invention will be discussed below with reference to FIGS. 1 to 4.

FIG. 1 is a plan view according to a first embodiment of the present invention. In particular, FIG. 1 shows a tracheal tube 10, having a proximal end or machine end portion 40, and a distal or patient end portion 20, which are connected along the length of the tube by an intermediate flexible portion 30. The distal end portion 20, of the tracheal tube 10, may be preshaped in a curved configuration, so as to correspond in shape with the patient's posterior pharynx and trachea. The distal end portion 20, terminates in a beveled end 60, having an outlet orifice 24. A standard Murphy eye 27, may be located on the long wall side of the beveled end 60.

The length of the tracheal tube will vary in accordance with the needs of a particular patient. Further, length and shape of the tracheal tube will vary depending on whether such tube is to be intubated nasally or orally. Several standard lengths and shapes may be provided wherein the lengths are chosen so as to conform as closely as possible to the shape of the posterior pharynx and trachea of a patient and the shape is chosen so as to allow for either nasal or oral intubation respectively.

The proximal end portion 40, of the tracheal tube 10, comprises a relatively straight segment of tubing which terminates in an inlet orifice adapted to receive a standard connector 70. Proximal end portion 40, has an outside diameter equivalent to that of distal end portion 20. The proximal end portion 40, may be connected to any suitable connectors and/or adapters for attachment to an anesthesia machine.

The distal end portion 20, and the proximal end portion 40, are each attached to intermediate portion 30. Intermediate portion 30, has an outside diameter equivalent to the outside diameters of both the distal end portion 20, and the proximal end portion 40. Intermediate portion 30, is formed of a material which resists kinking, and allows for complete movement and rotation of the proximal end portion 40, without a corresponding movement of distal end portion 20. By providing such a flexible intermediate portion 30, it is possible to relocate the proximal end portion 40, relative to the head and neck of a patient undergoing surgery, without the necessity of re-intubation and without producing undue stress on the distal end portion 20. Therefore the risk of injury or trauma to the patient's naris, mucosa and trachea may be minimized.

The intermediate portion 30, is attached to the distal end portion 20, and the proximal end portion 40, by any suitable means, such as, adhesives including glue or epoxy, connectors, compression fittings, insert molded connectors, heat bonding or molecular bonding. In FIG. 1, the attachment is accomplished by means of a connector 50.

Figure 3:
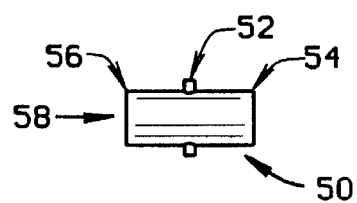
FIG. 3 is a cross sectional view of a connector which may be used in the tracheal tube according to the present invention.

A connector 50, is shown in cross section in FIG. 3 and comprises a through lumen 58, a first connection end 54, a second connection end 56, and a separation wall 52. The first and second connection ends 54 and 56, are sized so as to allow insertion thereof into the lumens of the distal end portion 20, proximal end portion 40, and intermediate portion 30, of the tracheal tube 10. The separation wall 52, has a greater outside diameter than either first or second connection ends 54 and 56. The outside diameter of separation wall 52, is formed to be equivalent to the outside diameter of the distal end portion 20, proximal end portion 40, and intermediate portion 30, of tracheal tube 10. In this way, when tracheal tube 10, is fully constructed, it will exhibit a uniform outside diameter along its entire length.

Figure 2:
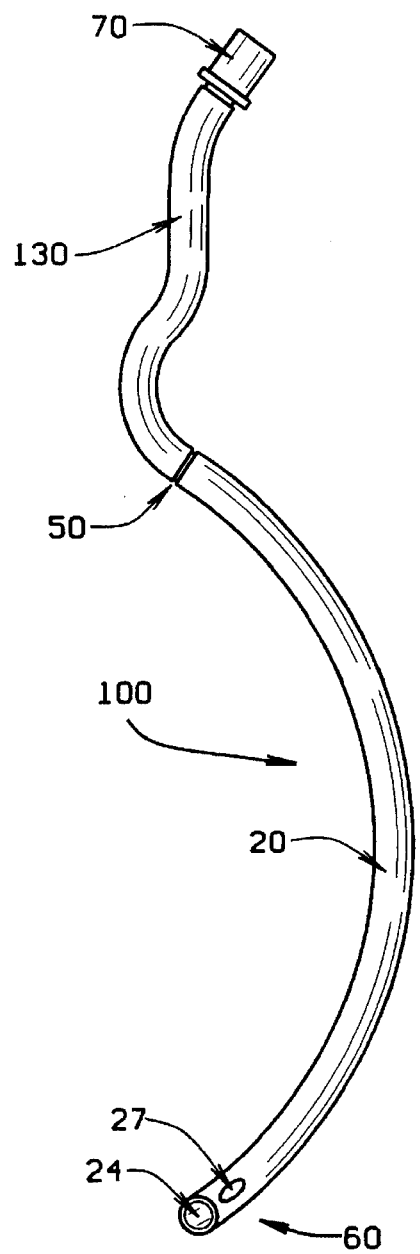
FIG. 2 is a plan view of a second embodiment of the tracheal tube according to the present invention.

FIG. 2 shows a plan view of a tracheal tube according to a second embodiment of the present invention, wherein features equivalent to those of tracheal tube 10, shown in FIG. 1, are identified by like reference numerals. As is clear from FIG. 2, tracheal tube 100, is comprised of only two portions; i.e. distal end portion 20, and flexible proximal end portion 130. This design simplifies construction of the tracheal tube 100, and provides the greatest flexibility at the proximal end.

The distal end portion 20, and the proximal end portion 40, of tracheal tube 10, may be preformed from any suitable material having sufficient memory or resilience to return to the preformed shape following flexure. In particular, the distal end portion 20, should be made of a material which enables it to conform to the posterior pharynx and trachea of the patient, rather than forcing the posterior pharynx and trachea to conform to the tracheal tube. Further, the material should be such that the distal end portion 20, and proximal end portion 40, retain their configuration and do not kink during use. Flexible thermoplastic materials such as polyvinylchloride, polyethylene, or the like are preferred materials meeting all of the above requirements.

Proximal end portion 40, may advantageously be formed of a clear thermoplastic material to provide for visual observation of breath condensation, which may be used to monitor the anesthesia procedure.

Flexible portion 30, or 130, may be formed of any suitable flexible material which allows for acute bends while maintaining constant connection to the other portions of the tracheal tube 10, or 100. This material must be capable of such bends without kinking or transferring unnecessary force to the proximal end portion 40, or the distal end portion 20, while maintaining constant inside and outside diameters. In a preferred embodiment, flexible portion 30, or 130, is formed from either expanded polytetrafluoroethylene (PTFE) tubing or a polyethylene material (any grade). Such a material is useful for forming a non-reinforced flexible tube.

In another embodiment of the present invention, the flexible portion 30, or 130, may be made of a flexible material having a reinforcing filament embedded therein. By using such a filament, it is possible to use a softer, more flexible material for the flexible portion 30, or 130, of the tracheal tube and to increase the stability and non-kinking attributes thereof. In particular, the flexible material may be a thermoplastic material, such as polyvinylchloride, polyethylene, or the like; an elastomer, such as latex, rubber, or silicone; or a thermoplastic elastomer such as polyurethane, krayton, santoprene, or the like.

In preferred embodiment all portions of the tracheal tube are made of polyvinylchloride having varying flexibility. In particular, the flexible portion 30, or 130, may be a polyvinylchloride which includes a relatively high percentage of plasticizer in its composition, thus making it more flexible and softer than the polyvinylchloride used for the other portions of the tracheal tube. However, by using a softer material composition for the flexible portion, that portion becomes more susceptible to kinking. Therefore, it is desirable to use a reinforcing filament as noted above to increase the stability and non-kinking attributes of the flexible portion. One advantage of this embodiment it that because the flexible portion 30, of 130, is of a similar material to the distal end portion 20, and the proximal end portion 40, bonding of the various portions may be accomplished without connectors which connectors may disadvantageously add to the outer diameter of the tracheal tube in the area of the connector.

Figure 4:
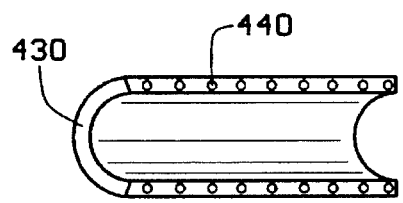
FIG. 4 is a cross sectional view of a portion of the tracheal tube according to a particular embodiment of the present invention.

FIG. 4 is a cross sectional view of a portion of the tracheal tube according to the embodiment of the present invention described above. In particular, the flexible portion is indicated by reference numeral 430, and is shown in cross section to show reinforcing filament 440. As noted above, the filament 440, provides greater stability and strength to the flexible portion 430.

The filament 440, may be made of any suitable material, including metal wires such as steel, copper, nickel, aluminum, brass or other metal alloys; plastic; or graphite. Preferably, the filament 440, is made of a hardened steel wire having shape retention characteristics.

The filament 440, is provided in such a manner that it is completely covered by the material of the flexible portion 430. In this way, the smooth inner lumen of the flexible portion 430, can be maintained. The flexible portion 430, with the filament 440, may be made by standard lamination and coextrusion processes. For example, a first thin layer of material may be laminated onto a mandril having a diameter equal to a desired inside diameter for the tracheal tube. The filament may then be laid down of the first layer of material in a spiral wind. Alternatively, the filament may be provided in a mesh pattern over the first layer of material. A thin adhesive coating which acts to hold the filament firmly in place may then be coated onto the first layer of material, and the entire substructure is then overlaid by a second layer of material to the reach the desired outside diameter of the tube.

The various tubing portions of the tracheal tube according to the present invention should have the same inside and outside diameters. Suitable inside diameters range from 3.0 mm to 9.0 mm, with corresponding outside diameters ranging from 4.3 mm to 12.1 mm.

The tracheal tube according to the present invention allows movement of the proximal end of the tracheal tube during anesthesiology and surgery without requiring re-intubation of the patient. In particular, the method of use according to the present invention consists of providing a specialized tracheal tube as described above, intubating the patient in a normal fashion such that the proximal end of the tracheal tube is established in an initial position relative to the head and neck of the patient, and moving the proximal end via the flexible portion of the tracheal tube to a second position relative to the head and neck of the patient, without re-intubation of the patient.

The design of the present invention makes it possible to use a tracheal tube and still allow 360 degree access to the head and neck area of a patient. In addition, the tracheal tube according to the present invention allows for movement of the proximal end of the tracheal tube during a surgical procedure, without requiring re-intubation. Therefore, even greater access to the surgical area is possible and is accomplished without increasing the risk of injury or trauma to the patient.

Use of the tracheal tube according to the present invention provides greater and more complete access to the head and neck area during surgery. Therefore, the surgeon may occupy any optimal location around the head of the patient, so that surgery may be completed successfully and with greater efficiency. Further, competition for space between the surgeon and anesthesiologist may be eliminated by using the tracheal tube according to the present invention.

Another advantage of the tracheal tube according to the present invention is that the flexible portion does not have shape-retaining properties, and therefore does not transmit stress to the distal end of the tracheal tube. This helps to reduce or avoid injury or trauma to the naris, mucosa and trachea of the patient.

A further advantage of the tracheal tube according to the present invention is the provision of a smooth constant diameter lumen throughout the length of the tracheal tube. This construction allows for ease of passage of instruments, such as, fiber optic scopes and suction catheters, for example, through the tracheal tube. In particular, there are no corrugated ridges for instruments to get hung-up on, as is possible in several prior art tracheal tubes.

The foregoing has been a description of certain preferred embodiments of the present invention, but is not intended to limit the invention in any way. Rather, many modifications, variations and changes in details may be made within the scope of the present invention.

What is claimed is:

1. A tracheal tube comprising a distal end portion for intubation into a patient;

a flexible intermediate portion smoothly merged with said distal end portion; and a proximal end portion smoothly merged with said intermediate portion;

wherein said tracheal tube has a smooth continuous lumen running the entire length of the tracheal tube;

wherein said flexible intermediate portion includes a reinforcing filament and is capable of withstanding acute bends without kinking;

and wherein said distal end portion and said proximal end portion are each attached to said intermediate portion, by a suitable means selected from the group consisting of adhesives, connectors, compression fittings, and insert molded connectors.

2. A tracheal tube according to claim 1, wherein said filament is provide in a spiral wind or in a mesh pattern.

3. A tracheal tube according to claim 1, wherein said distal end portion, said intermediate portion and said proximal end portion are each made of a thermoplastic material.

4. A tracheal tube according to claim 1, wherein said filament is made from a material selected from the group consisting of metal wires such as steel, copper, nickel, aluminum, brass or other metal alloys; plastic; or graphite.

5. A tracheal tube comprising a distal end portion for intubation into a patient; and a flexible proximal portion smoothly merged with said distal end portion;

wherein said tracheal tube has a smooth continuous lumen running the entire length of the tracheal tube;

wherein said flexible proximal portion includes a reinforcing filament and is capable of withstanding acute bends without kinking;

and wherein said distal end portion is attached to said flexible proximal portion, by a suitable means selected from the group consisting of adhesives, connectors, compression fittings, and insert molded connectors.

6. A tracheal tube according to claim 5, wherein said filament is provide in a spiral wind or in a mesh pattern.

7. A tracheal tube according to claim 5, wherein said distal end portion and said flexible proximal portion are both made of a thermoplastic material.

8. A tracheal tube according to claim 5, wherein said filament is made from a material selected from the group consisting of metal wires such as steel, copper, nickel, aluminum, brass or other metal alloys; plastic; or graphite.

* * * * *